United States Patent
Stokes

(10) Patent No.: US 8,546,773 B2
(45) Date of Patent: Oct. 1, 2013

(54) IRRADIATION SYSTEM AND METHOD

(76) Inventor: John P. Stokes, San Antonio, TX (US)

( * ) Notice: Subject to any disclaimer, the term of this patent is extended or adjusted under 35 U.S.C. 154(b) by 219 days.

(21) Appl. No.: 12/873,781

(22) Filed: Sep. 1, 2010

(65) Prior Publication Data

US 2011/0163245 A1   Jul. 7, 2011

Related U.S. Application Data

(60) Provisional application No. 61/239,346, filed on Sep. 2, 2009.

(51) Int. Cl.
*A61N 5/00* (2006.01)

(52) U.S. Cl.
USPC .............. 250/492.1; 250/492.3; 250/493.1; 250/505.1; 378/17; 378/21; 378/65; 378/193; 378/195

(58) Field of Classification Search
USPC ....... 250/492.1, 492.3, 493.1, 505.1; 378/17, 378/21, 65, 193, 195, 196
See application file for complete search history.

(56) References Cited

U.S. PATENT DOCUMENTS

| | | | |
|---|---|---|---|
| 6,984,835 B2 | 1/2006 | Harada | |
| 7,142,634 B2 * | 11/2006 | Engler et al. | 378/65 |
| 7,295,648 B2 * | 11/2007 | Brown | 378/65 |
| 7,616,735 B2 * | 11/2009 | Maciunas et al. | 378/69 |
| 2004/0162457 A1 | 8/2004 | Giorgio et al. | |
| 2004/0170254 A1 * | 9/2004 | Gregerson et al. | 378/197 |
| 2005/0089141 A1 * | 4/2005 | Brown | 378/65 |
| 2006/0193435 A1 | 8/2006 | Akatsu et al. | |
| 2007/0025509 A1 | 2/2007 | Bani-Hashemi et al. | |
| 2008/0317312 A1 | 12/2008 | Carl et al. | |
| 2009/0067579 A1 * | 3/2009 | Mansfield | 378/189 |
| 2009/0156881 A1 | 6/2009 | Stokes | |
| 2009/0209805 A1 | 8/2009 | Lubock et al. | |
| 2010/0202588 A1 * | 8/2010 | Shibuya et al. | 378/65 |

FOREIGN PATENT DOCUMENTS

| | | | |
|---|---|---|---|
| JP | 07265445 A | * | 10/1995 |
| WO | 2009/052187 | | 4/2009 |
| WO | 2011/028789 | | 3/2011 |

OTHER PUBLICATIONS

International Search Report and Written Opinion for PCT/US10/47509 mailed May 25, 2011.

* cited by examiner

*Primary Examiner* — Michael Logie
(74) *Attorney, Agent, or Firm* — Meyertons, Hood, Kivlin, Kowert & Goetzel, P.C.; Eric B. Meyertons

(57) ABSTRACT

A radiotherapy technique for providing a radiation source having a radiation path that intersects a treatment area, activating the radiation source, and moving the radiation source in three dimensions about the treatment area, wherein the radiation source is continually directed substantially toward an isocentric point within the treatment area.

23 Claims, 4 Drawing Sheets

IRRADIATION SYSTEM AND METHOD

PRIORITY

This application claims benefit of priority to U.S. Provisional Patent Application Ser. No. 61/239,346, entitled "IRRADIATION SYSTEM AND METHOD", filed Sep. 2, 2009, by John P. Stokes, which is hereby incorporated by reference in its entirety as though fully and completely set forth herein.

BACKGROUND

1. Field of the Invention

The present invention generally relates to systems and methods for irradiation and more particularly to homogeneous radiation distribution systems and methods.

2. Description of Related Art

Radiation therapy (also known as radiotherapy, radiosurgery or radiation oncology) is the medical use of ionizing radiation as part of cancer treatment to control malignant cells. Radiotherapy is used for the treatment of malignant tumors (cancer), and may be used as the primary therapy. It is also common to combine radiotherapy with surgery, chemotherapy, hormone therapy or some mixture of the three. Most common cancer types can be treated with radiotherapy in some way.

Radiotherapy may be used for different purposes, including curative or adjuvant cancer treatment. Radiotherapy is often used as palliative treatment (i.e., where cure is not possible and the aim is provide local disease control or symptomatic relief) or as therapeutic treatment (i.e., where the therapy has survival benefit and it can be curative). The precise treatment intent (e.g., curative, adjuvant, neoadjuvant, therapeutic, or palliative) will depend on the tumor type, location, and stage, as well as the general health of the patient.

Radiotherapy may include various techniques, such as Total body irradiation (TBI) which is used to prepare the body to receive a bone marrow transplant. Radiotherapy also has several applications in non-malignant conditions, such as the treatment of trigeminal neuralgia, severe thyroid eye disease, pterygium, pigmented villonodular synovitis, prevention of keloid scar growth, and prevention of heterotopic ossification. The use of radiotherapy in non-malignant conditions is limited partly by worries about the risk of radiation-induced cancers.

The amount of radiation used in radiation therapy is typically measured in gray (Gy), and varies depending on the type and stage of cancer being treated. For curative cases, the typical dose for a solid epithelial tumor ranges from 60 to 80 Gy, while lymphoma tumors are treated with 20 to 40 Gy. Preventative (adjuvant) doses are typically around 45-60 Gy in 1.8-2 Gy fractions (e.g., for breast, head and neck cancers). Many other factors are considered by radiation oncologists when selecting a dose, including whether the patient is receiving chemotherapy, whether radiation therapy is being administered before or after surgery, and the degree of success of surgery.

The total dose may be fractionated (spread out over time) for several important reasons. Fractionation allows normal cells time to recover, while tumor cells are generally less efficient in repair between fractions. Fractionation also allows tumor cells that were in a relatively radio-resistant phase of the cell cycle during one treatment to cycle into a sensitive phase of the cycle before the next fraction is given. Similarly, tumor cells that were chronically or acutely hypoxic (and therefore more radioresistant) may reoxygenate between fractions, improving the tumor cell kill.

Irradiation is the process by which an item is exposed to radiation. In common usage the term refers specifically to ionizing radiation, and to a controlled level of radiation that will serve that specific purpose, such as radiation therapy, rather than radiation exposure to normal levels of background radiation or abnormal levels of radiation due to accidental exposure.

During radiation therapy, it is desirable to provide the most effective dose to the treatment area (e.g., a tumor) while limiting any radiation exposure to healthy cells. Radiotherapy is commonly applied to the cancerous tumor and it is necessary to subject a margin of normal tissue around the tumor to radiation to allow for uncertainties in set-up and internal tumor motion. These uncertainties can be caused by internal movement (e.g., respiration and bladder filling) and movement of external skin marks relative to the tumor position. To spare normal tissues (e.g., skin or organs which radiation must pass through in order to treat the tumor), shaped radiation beams are aimed from several angles of exposure to intersect at the tumor, providing a much larger absorbed dose at the tumor than in the surrounding, healthy tissue. One technique for example includes the use of a gamma knife. A gamma knife device contains 201 cobalt-60 substantially fixed sources of approximately 30 curies (1.1 TBq) each, placed in a circular array in a heavily shielded assembly. The device aims gamma radiation through a target point in the patient's brain. The patient wears a specialized helmet that is surgically fixed to their skull such that the brain tumor remains stationary at target point of the gamma rays. An ablative dose of radiation is thereby sent through the tumor in one treatment session, while surrounding brain tissues are subject to reduced levels of radiation. Unfortunately, the gamma knife may still subject certain areas of normal tissue to increased radiation levels.

Accordingly, it is desirable to provide a technique for the irradiation to a treatment area while lowering the effective levels of irradiation of non-treatment areas, thereby treating the affected area while limiting damage to adjacent tissue.

SUMMARY

Various embodiments of irradiation systems and related apparatus, and methods of operating the same are described. In some embodiments, provided is a method of radiotherapy includes providing a radiation source having a radiation path that intersects an isocentric point and/or treatment area, activating the radiation source, moving the radiation source in a first circular path such that its radiation path continues to intersect the isocentric point and/or the treatment area, and moving the radiation source in a second circular path that is generally perpendicular to the first circular direction such that its radiation path continues to intersect the isocentric point and/or the treatment area.

In some embodiments, provided is irradiation system. The system includes a radiation source having a radiation path that intersects an isocentric point and/or treatment area. The radiation source is movable in a first circular path such that its radiation path continues to intersect the isocentric point and/or the treatment area. The radiation source is also movable in a second circular path that is generally perpendicular to the first circular direction such that its radiation path continues to intersect the isocentric point and/or the treatment area.

In some embodiments, provided is a method of radiotherapy, that includes activating a radiation source having a radiation path that intersects a treatment area, and moving the radiation source in three dimensions about the treatment area, wherein the radiation source is continually directed substantially toward an isocentric point within the treatment area.

In some embodiments, provided is an irradiation system that includes a radiation source having a radiation path that intersect an isocentric point and/or treatment area during use, and a supporting structure that, during use, moves the radiation source in three dimensions about the treatment area, such that the radiation source is continually directed substantially toward an isocentric point within the treatment area.

In some embodiments, provided is a non-transitory computer readable medium storing program instructions that when executed by a computer cause activating a radiation source having a radiation path that intersects a treatment area, and moving the radiation source in three dimensions about the treatment area, wherein the radiation source is continually directed substantially toward an isocentric point within the treatment area.

BRIEF DESCRIPTION OF THE DRAWINGS

Advantages of the present invention will become apparent to those skilled in the art with the benefit of the following detailed description and upon reference to the accompanying drawings in which.

Figure 1:
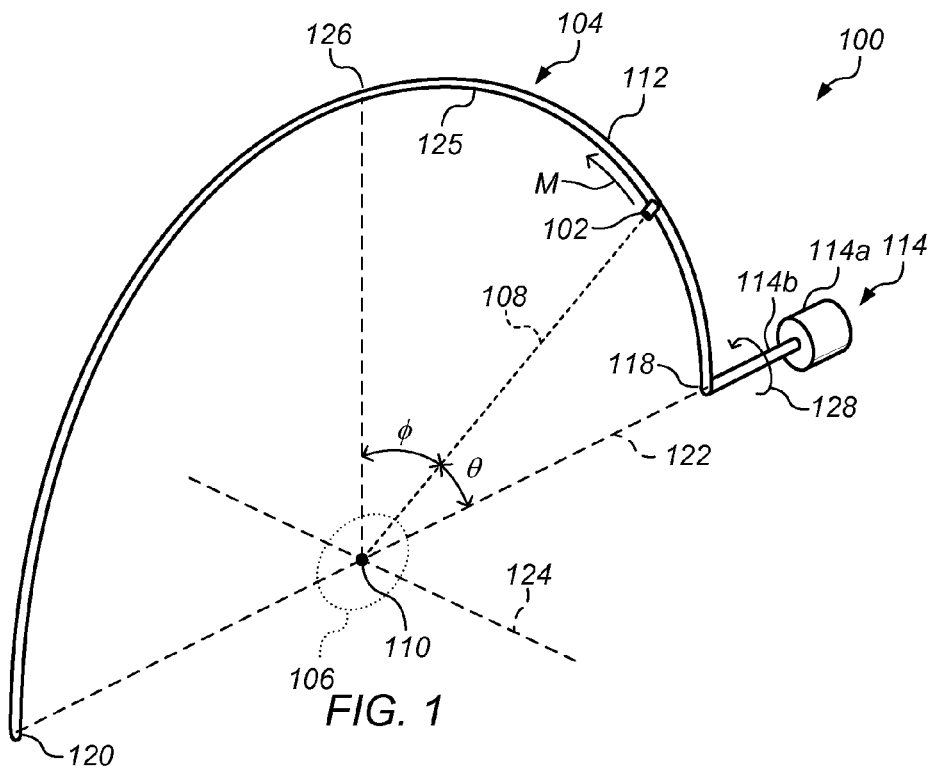
FIGS. 1-3 are diagrams that illustrate radiation treatment systems in accordance with one or more embodiments of the present technique.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF ILLUSTRATIVE EMBODIMENTS

As discussed in more detail below, embodiments of the present technique include a system and/or method for providing a radiation to a treatment area. In certain embodiments, the technique includes the use of a dynamic radiation source that can be moved relative to the treatment area. In some embodiments, the dynamic radiation source is moved around the treatment area while continuously directing its radiation beam toward and through the treatment area. In certain embodiments, the dynamic radiation source is moved around the treatment area such that radiation is provided from a variety of positions surrounding the treatment area, resulting in a plurality of radiation paths irradiating the treatment area from a variety of directions. In some embodiments, radiation may be provided from an increasing number, or even an infinite number, of points surrounding the treatment area. In some embodiments, the dynamic radiation source is moved (e.g., rotated) about the treatment area in three dimensions (e.g., about two axes) during use. In some embodiments, an irradiation system includes a gantry having an arc shaped guide that is rotatable about a first axis, and a radiation source that is moveable along the arc of the gantry about a second axis that is substantially normal to the first axis. In certain embodiments, a radiation beam generated by the radiation source is continually directed toward the treatment area as the guide is rotated and the dynamic radiation source is moved along the guide such that the combined simultaneous rotation of the gantry and movement of the radiation source results in a partial or complete spherical-helical or hemispherical-helical path of the radiation source about the treatment area. In some embodiments, the rotation of the gantry and/or movement of the radiation source are regulated to control radiation exposure of tissue surrounding the treatment area. In certain embodiments, the rate of the movement of the radiation source along the guide at a given point is regulated such that surrounding tissues of a similar proximity to an isocentric center of the treatment area (e.g., at a similar radius from the isocentric center of the treatment area) are subject to the same or about the same intensity of radiation. Certain embodiments provide for producing a field of radiation having radiation intensities that are constant (e.g., homogeneous) among all points located at a given distance/radius from the isocentric point, thereby resulting in substantially homogenous exposure to radiation of tissue at a given distance from the treatment area. Embodiments of the technique described herein may help to distribute the gamma radiation over a much larger volume of tissue as it is approaching the area to be treated and is, therefore, less likely to cause radiation damage to normal tissues surrounding the lesion to be treated. In effect, embodiments may divide the radiation into a large or even infinite number of beams, since it may distribute the radiation equal among all angles of approach to the isocentric center of the treatment area.

FIG. 1 depicts a radiation treatment system 100 in accordance with one or more embodiments of the present technique. In the illustrated embodiment, system 100 includes a dynamic radiation source 102 coupled to a gantry 104. Gantry 104 may include a supporting structure that physically supports and guides movement of radiation source 102 about a treatment area 106. Treatment area 106 may include, for example, the location of a tumor (e.g., a brain tumor of patient) or similar area of medical concern that may benefit from exposure to elevated levels of radiation associated with radiotherapy. As described in more detail below, radiation source 102 may be guided by gantry 104 to various positions surrounding treatment area 106 while simultaneously being directed to treatment area 106. For example, radiation source 102 may be moved along a portion of gantry 104, such as along a track running along its length, to provide radiation from a plurality of locations about a rotational axis containing gantry 104 and/or gantry 104 may be rotated about another rotational axis substantially normal to the other rotational axis such that radiation can be provided from radiation source 102 to treatment area 106 from a variety of different paths. In the illustrated embodiment, a single radiation source 102 is depicted. Other embodiments may include a plurality of radiation sources. For example, two or more radiation sources may be disposed on gantry 104.

Radiation source 102 may include a device capable of generating and/or directing radiation toward treatment area 106. Radiation source 102 may include, for instance, cobalt-60 source that generates a radiation beam/path 108, such as an electron beam, gamma rays, or the like. Radiation beam 108 may have a width that is substantially the same as a diameter of treatment area 106. In some embodiments, radiation source 102 may include additional devices configured to regulate and direct radiation. For example, radiation source 102 may include one or more collimators. Collimators may be employed to focus radiation beam 108 into a narrow target, such as small/narrow treatment area 106. Radiation beam 108 may be directed from radiation source 102 toward an isocentric point 110 of target area 106 during use. Isocentric point 110 may include a point where a path of radiation beam 108 is continually focused as radiation source 102 moves. Isocentric point 110 may typically be located within treatment area 106, and may be located centrally within treatment area 106. For example, during treatment of a brain tumor, a patient's skull may be fixed such that tumor remains still, and one or more radiation sources may be aimed at an isocentric point at a center of the tumor such that the generated radiation beams pass though the skull and brain and into the tumor.

In some embodiments, radiation source 102 may be movable such that radiation beam 108 can be directed toward treatment area 106 from a variety of positions. Such an embodiment may enable and increased and intense dosage of radiation to be delivered to target area 106 from numerous radiation paths, thereby reducing the radiation exposure of one or more portions of tissue surrounding treatment area 106. This reduction in radiation exposure to surrounding tissue may be attributed to the distribution of radiation to treatment area 106 via numerous path locations, as opposed to a limited number of paths used to deliver the a similar dose of radiation to treatment area 106. In other words, radiation may be distributed throughout the surrounding tissue such that one portion of the tissue does not experience a high amount of exposure with respect to the other surrounding portions of tissue.

In some embodiments, radiation source 102 may be positioned anywhere along a spherical or hemispherical region surrounding isocentric point 110 during use. For example, radiation source 102 may be moved in three dimensions about isocentric point 110 at a substantially constant distance, thereby following a substantially spherical/hemispherical three dimensional path about isocentric point 110. In each of the positions along the three dimensional spherical or hemispherical path surrounding isocentric point 110, radiation source 102 may be directed toward isocentric point 110 such that radiation beam 108 is continually directed through isocentric point 110 and/or treatment area 106. Accordingly, radiation source 108 may be used to provide radiation from some or substantially all positions surrounding isocentric point 110. In some embodiments radiation source 102 may have its position varied via rotation about two axes that are normal to one another. In some embodiments variations are provided in both axes simultaneously to provide an at least partial spherical-helical path about isocentric point 110 and treatment area 106, as described herein.

In some embodiments, movement of radiation source 102 may be guided by a supporting structure, such as gantry 104. In some embodiments, gantry 104 includes a guide 112 and drive unit 114. Guide 112 may include a rigid frame that physically supports radiation source 102 and guides its movement about isocentric point 110. Drive unit 114 may include a motor or similar motive device that provides for the movement of gantry 104 and/or radiation source 102.

In some embodiments, guide 112 includes a semi-circular, arch-shape structure. In the illustrated embodiment, for example, guide 112 includes an arch shaped member extending about one-hundred eighty degrees from a first end 118 to a second end 120. Curvature of guide 112 may be geometrically centered about isocentric point 110. For example, guide 112 may include a substantially circular arched shape having a substantially constant radius centered about isocentric point 110. First end 118, second end 120 and isocentric center 110 may substantially align along a first rotational axis 122. Guide 112 may have an arched shape curvature about a second rotational axis 124 passing through isocentric point 110 and substantially normal to first rotational axis 122. During use, guide 112 may be used to guide movement of radiation source 102 along its length in substantially the same arched shape path about second rotational axis 124, as indicated by arrow (M). In some embodiments, guide 112 includes a channel/track that enables source 102 to be coupled to and travel along a length of guide 112 between first end 118 and second end 120 of guide 112. During use, source 102 may move along the channel/track in an arched path 125 along an interior of guide 112, as indicated by arrow (M). Movement of radiation source 102 along guide 112 may be accomplished via an electrical motor, magnetic mechanism, or other motive device. As discussed in more detail below, the rate of movement of radiation source 102 along guide 112 may be regulated to provide a desired rate of movement of radiation source 102 relative to isocentric point 10 and/or treatment area 106.

In some embodiments, guide 112 may be substantially semi-circular in shape, having a curvature about isocentric point 110. Radiation source 102 may travel along guide 112 such that it travels in an arched/circular path about second rotational axis 124, isocentric point 110 and/or treatment area 106. A circular path may be provided to ensure that radiation source 102 and path 108 is continually directed toward isocentric point 110 as it travels along guide 112. Other embodiments may include various shaped supporting structures and/or techniques to ensure radiation source 102 is continually directed toward isocentric point 110. For example, radiation source 102 may be pivoted or other wise positioned such that path 108 is directed through isocentric point 110 and/or treatment area 106 as radiation source 102 is moved about isocentric point 110 and/or treatment area 106 regardless of the shape of guide 112.

In some embodiments, guide 112 may rotate about first rotational axis 122, as illustrated by arrow 128. During a full rotation of guide 112 about first rotational axis 122, ends 118 and 120 may remain in a relatively constant position, while guide 112 and its apex 126 may revolve over three hundred sixty degrees about first axis 122, thereby resulting in a spherical sweep of about isocentric point 110 and/or treatment area 106. Where a substantially full rotational sweep is provided, an area surrounding the treatment area 106 (e.g., the patient's body) may need to be free of obstructions to enable an unobstructed rotation of guide 112. In other embodiments, guide may not be moved in a full sweeping motion. For example, guide 112 may be oscillated back and forth in a partial sweep. In one such embodiment, a partial sweep of guide 112 includes a rotation of about one hundred eighty degrees about first axis 122, resulting in a substantially hemispherical sweep. During a sweep of guide 112, radiation source 102 may also be rotated about first rotational axis 122.

In some embodiments, guide 112 may be rotatable about first rotational axis 122 in coordination with movement of radiation source 102 along guide 112 about second axis 124. Movement of radiation source 102 along guide 112 about second axis 124 and/or rotation of guide 112 about first axis 122 may enable radiation source 102 to be positioned in a plurality of locations surrounding treatment area 106 while still enabling radiation beam 108 to be directed to isocentric point 110 via any number of paths. Variations of the position of radiation source 102 about first and second rotational axes 122 and 124 via movement along guide 112 and/or rotation of guide 112 may enable radiation source 102 to be located anywhere along a spherical or hemispherical region surrounding isocentric point 110. For example, guide 112 may be rotated about first rotational axis 122 simultaneous with movement of radiation source 102 along guide 112 about second rotational axis 124 to move radiation source in a spherical/hemispherical helical pattern about treatment area 106, as discussed in more detail below with respect to FIGS. 5 and 6. In each of the positions along the spherical or hemispherical region surrounding isocentric point 110, radiation source 102 may be directed toward isocentric point 110 and/or treatment area 106 such that radiation beam 108 is continually directed through isocentric point 110 and/or treatment area 106. Accordingly, radiation source 108 may be moved in a three-dimensional spherical path to provide radiation from substantially all positions surrounding isocentric point 110.

Drive unit 114 may provide motive force for rotation of guide 112 about first rotational axis 122. In the illustrated embodiment, drive unit 114 includes a drive 114a and a drive shaft 114b coupled between first end 118 and drive 114a. Drive 114a may include an electric motor and/or motor controller. Drive shaft 114b may include a rigid shaft that is capable of transferring torque from drive 114a to guide 112. In some embodiments, one or both of drive 114a and drive shaft 114b may include gearing or a transmission to provide for regulation of torque transmitted to gantry 104.

In the illustrated embodiment, guide 112 extends about one-hundred eighty degrees about second axis 124. Other embodiments may include a guide 112 that extends more or less than one hundred eighty degrees. For example, guide 112 may extend only about ninety degrees from first end 118 to apex 126. In such an embodiment, during rotation of guide 112, apex 126 may travel in a circular path about first rotational axis 121, resulting in a hemispherical sweep about isocentric point 110. Such a technique may be of particular use where it is difficult to limit obstructions about treatment area 106. For example, where a patient having a brain tumor is secured to a table or surface, the patient's head and body may be advanced to isocentric point 110 from an open end of guide 112 (e.g., opposite drive 114 in the depicted embodiment).

Figure 2:
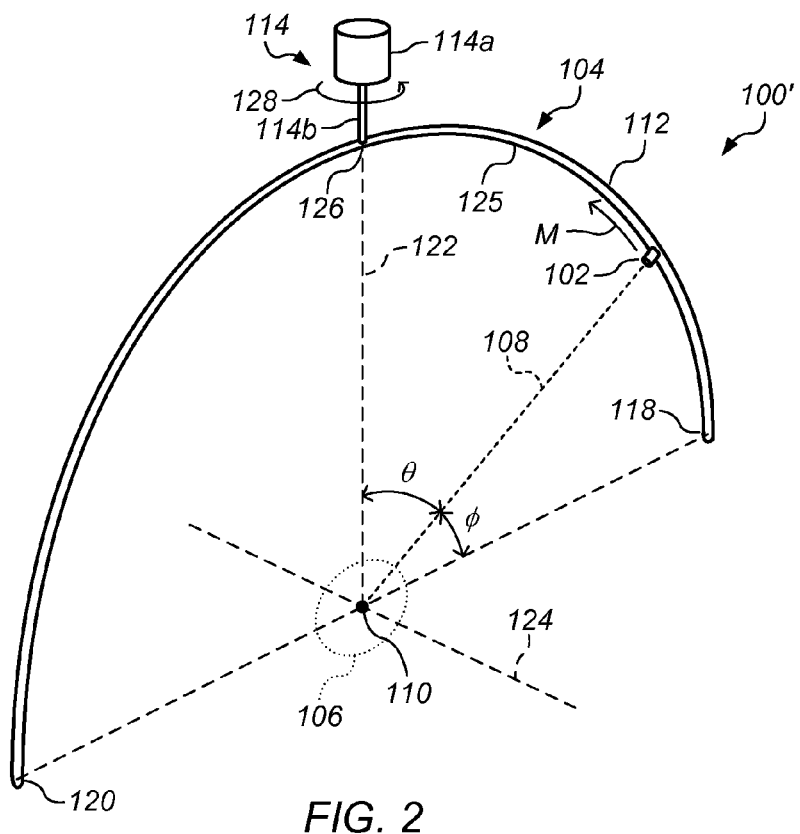

FIG. 2 depicts an embodiment of system 100' in accordance with one or more embodiments, of the present technique. System 100' may be similar to that of system 100. In the illustrated embodiment, system 100' includes gantry 104 arranged such that first rotational axis 122 passes through apex 126 of guide 112 and isocentric point 110. In such an embodiment, during rotation of guide 112, apex 126 may remain in a relatively constant in position, and ends 118 and 120 of guide 112 may travel in a substantially circular path, resulting in a hemispherical sweep of guide 112 about isocentric point 110. Such a technique may be of particular use where it is difficult to limit obstructions about a target area 106. In some embodiments, radiation source 102 may be moved along guide 112 about second rotational axis 124 (e.g., from first end 118 to apex 126 or second end 120, or vice versa) in a manner similar to that described above with respect to FIG. 1. For example, radiation source 102 may be moved along guide 112 in the direction of arrow (M) in coordination with rotation of guide 112 about first axis 122.

During rotation of guide 112, apex 126 may remain in a relatively constant position, and ends 118 and 120 of guide 112 may travel in a substantially circular path, resulting in a hemispherical sweep of guide 112 about isocentric point 110. Such a technique may be of particular use where it is difficult to limit obstructions about a target area 106. In some embodiments, radiation source 102 may be moved along guide 112 (e.g., from first end 118 to apex 126 or second end 120, or vice versa) in a manner similar to that described above with respect to FIG. 1. For example, radiation source 102 may be moved along guide 112 in the direction of arrow (M) in coordination with rotation of guide 112 about first axis 122.

Figure 3:
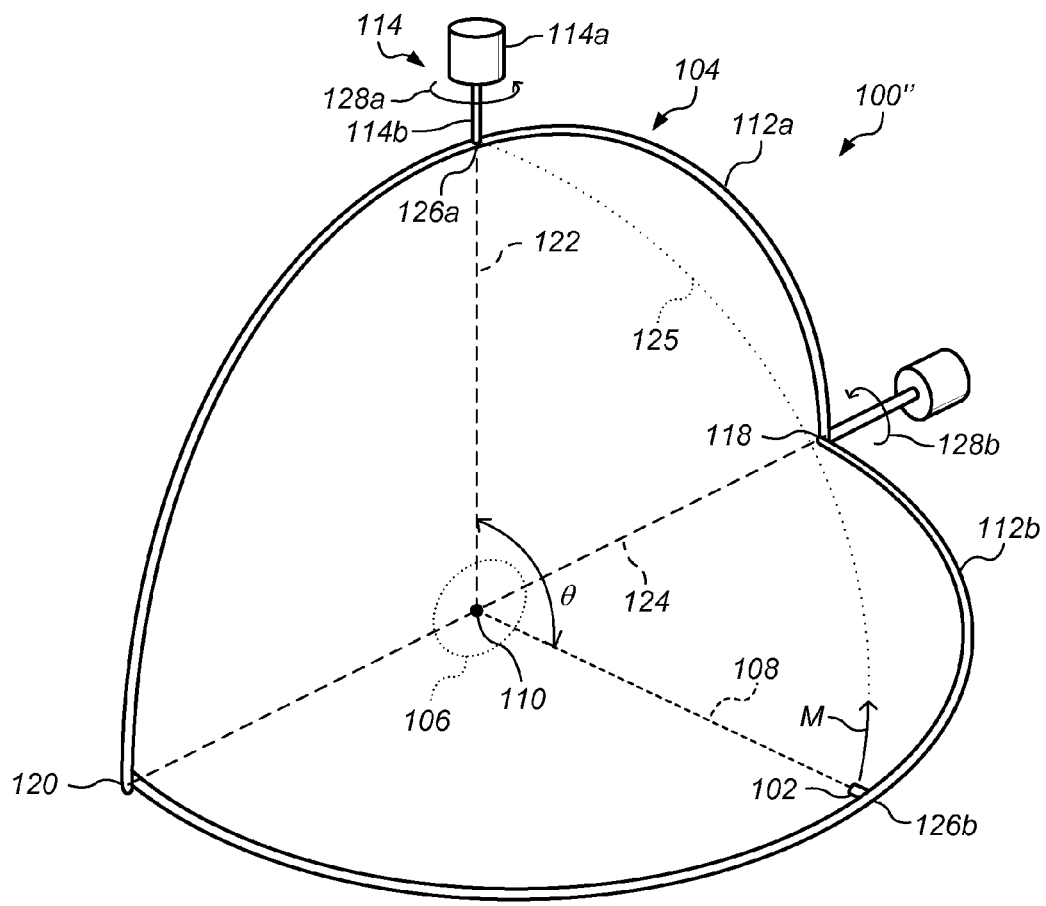
Figure 4A:
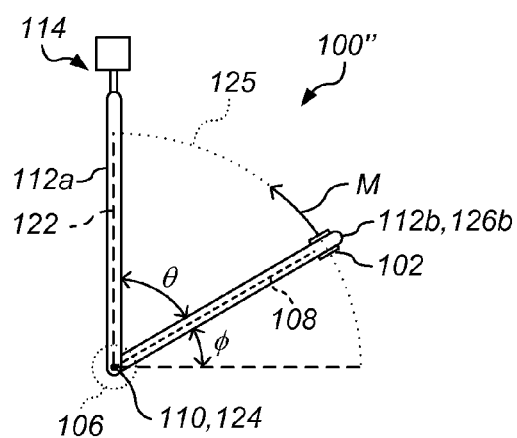
FIG. 4A illustrates a side-view of the system of FIG. 3 in accordance with one or more embodiments of the present technique.

FIG. 3 depicts an embodiment of a system 100" in accordance with one or more embodiments of the present technique. FIG. 4A illustrates a side-view of the system 100" of FIG. 3 in accordance with one or more embodiments of the present technique. In the illustrated embodiment, system 100" includes gantry 104 having a first guide member 112a and a second guide member 112b. First guide member 112a may be similar to that of guide member 112 described above with respect to FIGS. 1 and 2. First guide member 112a may include first end 118, second end 120, an apex 126a and drive unit 114 coupled thereto. Guide member 112a may rotate about first rotational axis 122 in a similar manner as that described above with respect to FIG. 2. In some embodiments, guide member 112a may not include radiation source 102 coupled thereto and may not include a track for the advancement of radiation source 102 there along. Second guide member 112b may include an arch shaped guide member that extends at least partially between first and second ends 118 and 120, having an apex 126b. Radiation source 102 may be coupled to second guide member 112b. During use, second guide member 112a may be swept/rotated about a second rotational axis 124 that is normal to first rotational axis 122, as illustrated by arrow 128b. In some embodiments, rotation of second guide member a 112b about may be provided via a second motor coupled to first end 118.

Radiation source 102 may be fixed at an apex 126a of second guide member 112b. Rotation of second guide member 112b about second rotational axis 124 may cause radiation source to move in the direction of arrow (M) in an arched path. The resulting arched path in the direction of arrow (M) may be the same or similar to that of the path (M) along guide 112 described with respect to FIGS. 1 and 2. In the illustrated embodiment of FIG. 4A, second member 112b is illustrated as sweeping about ninety degrees along path 125 between the horizontal and vertical axes. Such a sweep, when combined with rotation of guide member 112a about first rotational axis 122 may provide for movement of radiation source 102 in a hemispherical-helical path similar to that described with respect to FIG. 2. Other embodiments may include any sweep angle. For example, second guide member 112b and radiation source 102 may make a complete revolution of three-hundred sixty degrees about isocentric point 110 and second rotational axis 124. In some embodiments, second guide member 112b and radiation source 102 may make a partial rotation, such as an approximately half sweep of about one-hundred eighty degrees from a position where second guide member is about parallel to first rotational axis 122 and is rotated about one-hundred eighty degrees until it is again about parallel to first rotational axis 122. For example, with regard to FIG. 4A, second member 112b may move from being positioned pointing downward to pointing upward. Such a sweep, when combined with rotation of guide member 112a about first rotational axis 122 may have a spherical-helical path similar to that described with respect to FIG. 1.

In some embodiments, second guide member 112b and radiation source radiation source 102 may be rotated about second rotational axis 124 (e.g., in the direction of arrow M) in coordination with rotation of first guide 112a about first rotational axis 122. Rotation of second guide member 112b and radiation source 102 about second rotational axis 124 and/or rotation of guide 112a about first rotational axis 122 may enable radiation source 102 to be positioned in a plurality of locations surrounding treatment area 106 while still enabling radiation beam 108 to be directed to isocentric point 110 via any number of paths. Variations of the position of radiation source 102 about first and second rotational axes 122 and 124 via rotation of guide members 112a and/or 112b may enable radiation source 102 to be located anywhere along a spherical or hemispherical region surrounding isocentric point 110. For example, first guide member 112a may be rotated about first rotational axis 122 simultaneous with movement of radiation source 102 and second guide member 112b about second rotational axis 124 to move radiation source 102 in a spherical/hemispherical helical pattern about treatment area 106, as discussed in more detail below with respect to FIGS. 5 and 6. In each of the positions along the spherical or hemispherical region surrounding isocentric point 110, radiation source 102 may be directed toward isocentric point 110 and/or treatment area 106 such that radiation beam 108 is continually directed through isocentric point 110 and/or treatment area 106. Accordingly, radiation source 102 may be used to provide radiation from substantially all positions surrounding isocentric point 110.

Figure 4B:
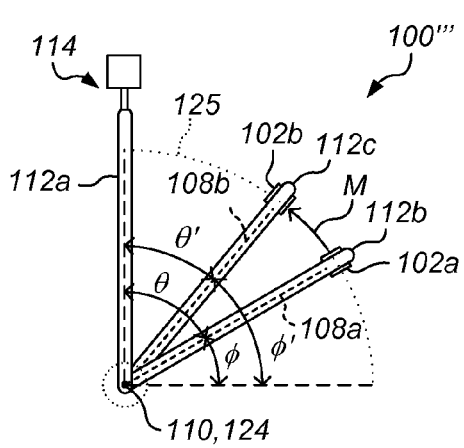
FIGS. 4B and 4C illustrate side-views of alternate systems in accordance with one or more embodiments of the present technique.
Figure 4C:
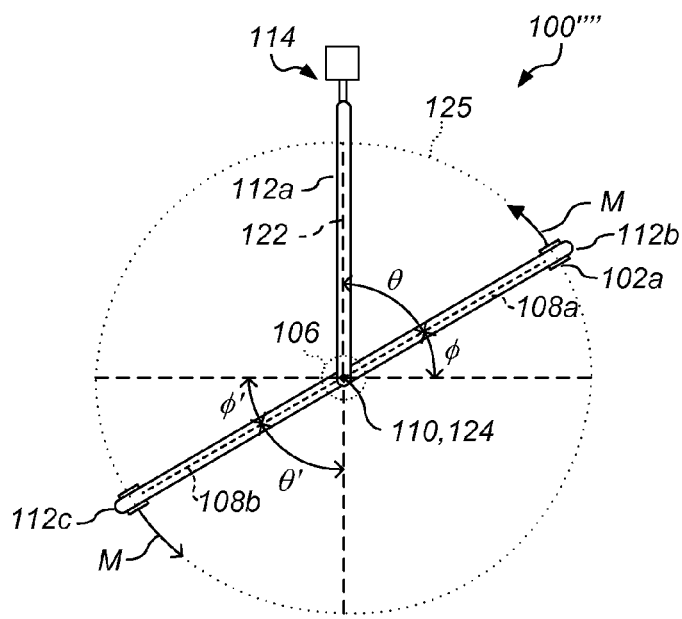

In some embodiments, a plurality of radiation sources 102 may be provided. FIG. 4B depicts an embodiment of system 100 having a plurality of radiation sources 102a and 102b in accordance with one or more embodiments of the present technique. System 100''' is similar to that of system 100'' described with respect to FIG. 3. In some embodiments, system 100''' includes first guide member 112a, second guide member 112b and a third guide member 112c. Second guide member may be similar to that of guide member 112b described above, including a radiation source 102a having radiation beam 108c. Third guide member 112c may be similar to that of second guide member 112b. For example, third guide member 112c may include a radiation source 102b having a radiation beam 108a that is continually directed through isocentric point 110 as first guide member 112a is rotated about first rotational axis 122a, second guide member 112b is rotated about second rotational axis 124 and/or third guide member is rotated about second rotational axis 124. In some embodiments, second and third guide members 112b and 112c may be simultaneously rotated about second rotational axis 124. In some embodiments, a rate of rotation of second and third guide members 112b and 112c may be varied based on their relative positions (e.g., an angle relative to first rotational axis 122), as described in more detail below. In some embodiments, each of second and third guide members 112b and 112c may be rotated at different rates to account for their different positions relative to first rotational axis 122a at a given time. For example, with respect to FIG. 4B, second and third guide members 112b and 112c may be rotated at different rates to account for their different angular positions (θ, φ, θ' and φ') relative to first rotational axis 122. In some embodiments, each of second and third guide members 112b and 112c may be rotated at the same rate. For example, with respect to system 100'''' of FIG. 4C, second and third guide members 112b and 112c may be rotated at the same rates as their respective angular positions (θ and θ', and φ and φ') relative to first rotational axis 122 are the same. Other embodiments may include any number of guide members having different or similar angular relations to first rotational axis 122a.

Figure 5:
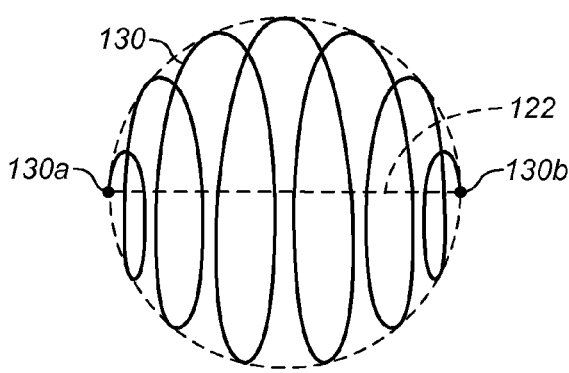
FIGS. 5 and 6 are diagrams that illustrate three-dimensional paths of a radiation source in accordance with one or more embodiments of the present technique.

As discussed above, in certain embodiments, radiation source 102 may be moved in coordination about first and second rotational axes. For example, radiation source 102 may be moved along guide 112 or rotated with second and/or third guide members 112b/112c about second rotational axis 124 in coordination with rotation of guide 112/112a about first rotational axis 122. In some embodiments, during treatment, radiation source 102 may move along a length of guide 112. For example, with respect to FIG. 1, source 102 may be positioned at or near first end 118, and may be advanced along guide 112 to second end 120 in direction (M) as guide 112 is rotated about axis 121. Similarly, with respect to FIGS. 3, 4, 4A and 4B guide member 112b/112c may be swept about one hundred eighty degrees between first and second positions parallel with first rotational axis 122. Such techniques may result in radiation source being moved in a spherical-helical path. FIG. 5 depicts an exemplary three-dimensional helical-spherical radiation source path 130 in accordance with one or more embodiments of the present technique. In the illustrated embodiment, path 130 includes a helical spiral that follows a substantially spherical shaped path about isocentric point 110 and treatment area 106 from a start point 130a to an end point 130b (or vice versa) about rotational axis 122. As discussed in more detail below, the rate of movement of source 102 about second rotational axis 124 may be regulated to vary the density of path 130. For example, radiation source 102 may be moved at a varying rate such that the total velocity relative to isocentric point 110 and/or treatment area 106 (e.g., the velocity due to the combination of rotation about first and second rotational axes 122 and 124) remains substantially constant. Such a constant velocity may help to provide homogeneous exposure to tissue at or neat treatment area 106.

In some embodiments, the rate of speed varies based on an angle theta (θ) of radiation beam 108 relative to first rotational axis 122. For example, with respect to FIG. 1, source 102 may be moved at a faster rate along guide 112 proximate ends 118 and 120 and at a slower rate proximate apex 126, or vice versa. Similarly, with respect to FIGS. 3, 4A, 4B and 4C, as guide member 112b is swept about one hundred eighty degrees between first and second positions parallel with first rotational axis 122, the guide member 112b may be rotated about second rotational axis 124 at a higher rate closer to each of the first and second positions. In some embodiments, the rotational rate of guide 112 may be increased or decreased relative to the rate of movement of radiation source 102 to further regulate the density of path 130. For example, guide 112/112a may be rotated at a high rate relative to the movement of source 102 about second rotational axis 124 such that there is a relatively small incremental movement of source 102 about second rotational axis 124 for each revolution of guide 112, thereby increasing the density of the path 130 (e.g., reducing the spacing between discrete radiation paths).

Figure 6:
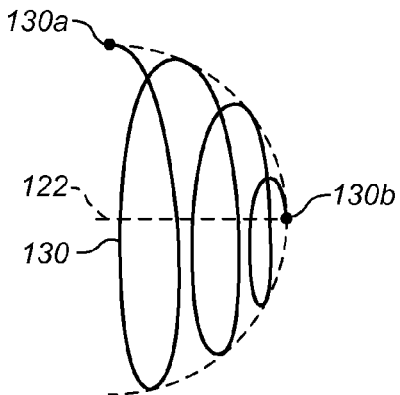

Some embodiments may provide for a helical path 130 that is not a substantially complete sphere. FIG. 6 depicts an exemplary three-dimensional hemispherical-helical radiation source path 130 in accordance with one or more embodiments of the present technique. In some embodiments, a semi-spherical or hemispherical helical sweep may be conducted. For example, with respect to FIG. 1, source 102 may be positioned at or near first end 118, and may be advanced along guide 112 to apex 126 as guide 112 is rotated about axis 121. Such a technique may result in a hemispherical-helical shaped path of radiation source 108. A similar technique may be employed with respect to the embodiments depicted in FIGS. 2-4C. For example, with regard to FIG. 2, source may be moved along guide 112 anywhere between any combination of first end 118, second end 120, and/or apex 126. With regard to FIGS. 3-4C, second guide member 112b and radiation source 102 may be swept approximately ninety degrees (e.g., from a horizontal to vertical positions as depicted in FIG. 4A).

As discussed in more detail below, the rate of movement of source 102 about second rotational axis 124 may be regulated to vary the density of path 130. In some embodiments, movement of radiation source 102 includes varying the rate of movement of radiation source 102 such that the radiation intensity exposure is substantially constant along substantially all locations a given radius from the isocentric center point 110. In certain embodiments, a rate of movement of source 102 may be varied based on its position with respect to first rotational axis 122. Radiation source 102 may be moved at a varying rate such that the total velocity (e.g., the velocity due to the combination of rotation about first and second axes 122 and 124) remains substantially constant. Such a constant velocity may help to provide homogeneous exposure to tissue at or neat treatment area 106. In some embodiments, the rate of speed varies based on an angle theta ($\theta$) of radiation beam 108 relative to first rotational axis 122, as discussed above and more detail below. For example, with respect to FIGS. 2 and 3, source 102 may be moved at a faster rate along guide 112 proximate apex 126 and at a slower rate proximate ends 118 and 120, or vice versa.

Figure 7:
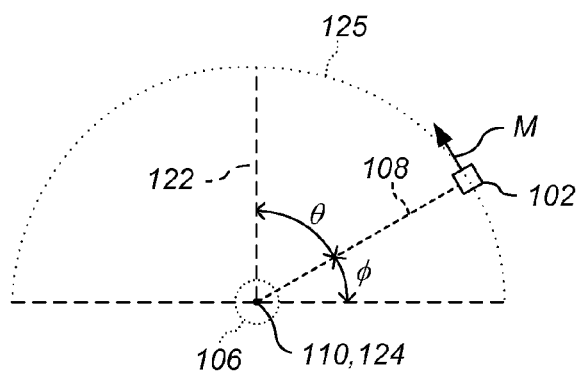
FIG. 7 is a diagram that illustrates an arched path of a radiation source in accordance with one or more embodiments of the present technique.

FIG. 7 illustrates positioning of radiation source 102 relative to first and second rotational axes 122 and 124 in accordance with one or more embodiments of the present technique. In the illustrated embodiment, radiation beam 108 extends from source 102 to treatment area 106 and isocentric point 110. First rotational axis 122 extends from isocentric center 110 and second rotational axis 124 passes through isocentric center 110 in a direction perpendicular to the sheet of paper. An angle theta ($\theta$) is located about isocentric point 110, between first rotational axis 122 and radiation source 102. For example, angle theta ($\theta$) is formed between radiation beam 108 and first rotational axis 122 as radiation source 102 is moved along path 125 about isocentric center 110. Angle phi ($\phi$) is complementary to angle theta ($\theta$).

In one embodiment, the rate of movement of radiation source 102 along path 125 in the direction of a vector (M) is inversely proportional to the sine of the angle theta ($\theta$) formed between first rotational axis 122 and radiation source 102 about isocentric center 110 and/or treatment area 106. Thus, the rate of movement of radiation source 102 may be inversely proportional to the cosine value of the angle phi ($\phi$) The rate of movement about second rotational axis 124 (e.g., the rate of movement along arched path 125) may be expressed as:

$$\text{Rate} = S * \frac{1}{\sin\theta} \quad (1)$$

Or $$\text{Rate} = S * \frac{1}{\cos\phi} \quad (2)$$

Where S is representative of a given speed and rate is a proportion of the speed. Accordingly, a speed for movement of radiation source 102 about second rotational axis 124 (e.g., the rate of movement along arched path 125) may be based on equations (1) and (2). Thus, in certain embodiments, the time spent by source 102 at a given angular position theta ($\theta$) is directly proportional to the value of sine ($\theta$), and the time spent by source 102 at a given angular position phi ($\phi$) is directly proportional to the value of cosine ($\phi$).

Radiation source 102 may have a higher velocity at or near first rotational axis 122. This may have an effect of producing a field of radiation in which the radiation intensity is constant along all or substantially all portions of a given radius from isocentric point 110. In certain embodiments, the above rate of rotation of guide 112 may be relatively constant. For example, guide 112 may rotate about axis 121 at a fixed rate during the period when source 102 is moved along guide 112.

In certain embodiments, system 100 produces a spherical field of radiation centered at a central point (e.g., isocentric point 110). Surrounding the center point is a small spherical area (e.g., treatment area 106) equal in diameter to a width of the radiation treatment beam (e.g., radiation beam 108 generated by source 102). Within this sphere, the radiation may be substantially homogenous and equal at all points. Outside of this sphere, the radiation intensity is equal for all points at a constant distance from the center. These can be thought of as concentric, spherical shells surrounding the treatment point. The intensity of radiation is constant all over the surface of a given shell, because all points of the shell are an equal distance (e.g., the radius of the shell) from the central treatment point. In one embodiment, the ratio of irradiation intensity at any point at a distance $R_2$ from the isocentric point to the intensity at the edge of the targeted treatment area of radius $R_1$, will be equal to $(R_1^2)/(R_2^2)$ since the surface area of a sphere is proportional to the square of its radius.

Figure 8:
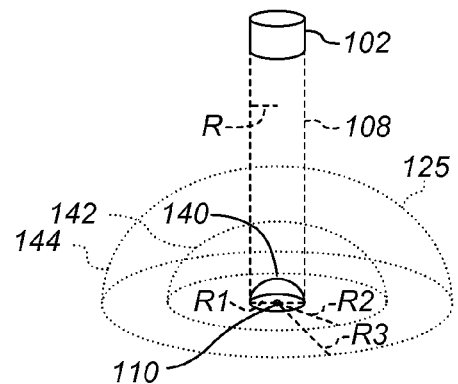
FIG. 8 is a diagram that illustrates radiation distribution in accordance with one or more embodiments of the present technique.

FIG. 8 illustrates hemispheres surrounding isocentric center 110 in accordance with one or more embodiments of the present technique. Although depicted as hemispheres for clarity, it will be appreciated that similar conditions may extends about isocentric center in a spherical shape/pattern. These hemispheres may be representative of all or a portion of radiation intensities that may be provided about an isocentric point in accordance with one or more embodiments of the present technique. In the illustrated embodiment, a treatment beam (e.g., radiation beam 108) having a radius (R) extends from source 102 to isocentric center 110. In the illustrated embodiment, a first hemisphere 140 has a radius ($R_1$) that is equal to radius R of treatment beam 108, a second hemisphere 142 has a second radius ($R_2$) that is greater that the first radius ($R_1$), and a third hemisphere 144 has a third radius ($R_3$) that is greater than second radius ($R_2$). First hemisphere may be indicative of half of a treatment area 106. The resulting radiation intensity may be uniform throughout first hemisphere radius having a radius R1. The radiation intensity may be constant across the surface of any hemisphere centered at isocentric center 110. The ratio of irradiation intensity at any point at a distance $R_2$ from the isocentric point to the intensity at the edge of the targeted treatment area of radius $R_1$, will be equal to the ratio of $(R_1^2)/(R_2^2)$, since the surface area of a sphere is proportional to the square of its radius. Expressed another way, the intensity of the radiation along a hemisphere shell of radius R will be the following:

$$\text{Intensity} = \left[ (R_{in}) x \left( \frac{R_1^2}{R^2} \right) \right] \quad (3)$$

Where $R_{in}$ is the intensity at the edge of the targeted treatment area of radius $R_1$.

FIG. 6 is a flowchart that illustrates a method 200 of irradiation in accordance with one or more embodiments of the present technique. Method 200 may be employed one or more techniques described herein with respect to systems 100, 100", 100''', and/or 100"", described herein. In some embodiments, method 200 includes providing a radiation source, as depicted at block 202. In one embodiment, providing a radiation source may include providing one or more radiation sources 102 coupled to a guide 112/112a/112b/112c of a gantry 104. In one embodiment, providing a radiation source may include positioning radiation source 102 such that its radiation path 108 intersects an isocentric point 110 and/or a treatment area 106.

In some embodiments, method 200 includes activating the radiation source, as depicted at block 204. In one embodiment, activating the radiation source includes activating one more radiation sources 102/102a/102b to deliver one or more radiation beams 108/108a/108b that intersects isocentric center 110 and/or treatment area 106. For example, radiation beam 108 may be directed on a path through a surrounding tissue and into treatment area 106.

In some embodiments, method 200 includes moving the radiation source, as depicted at block 206. Moving the radiation source may include moving one or more radiation sources 102/102a/102b in three dimensions about isocentric point 110 and/or treatment area 106 such that radiation beams 108/108a/108b of radiation source 102 is continually directed toward isocentric point 110 and/or treatment area 106. In some embodiments, moving the radiation source may include moving the radiation source in a first circular path such that its radiation path continues to intersect the isocentric center and/or the treatment area. For example, each radiation source 102/102a/102b may be moved in a substantially arched (e.g., circular) path about first rotational axis 122 passing through the isocentric point 110 such that radiation beam 108 continues to intersect isocentric point 110 and/or the treatment area 106. Further, each radiation source 102/102a/102b may be moved in a substantially arched (e.g., circular) path about second rotational axis 124 passing through the isocentric point 110 and substantially normal to the first rotational axis 124 such that the radiation beam 108 continues to intersect the isocentric point 110 and/or the treatment area 106. In some embodiments, moving the radiation source in a first circular path may include moving radiation source 102 along an arched member, such as guide 112 of the gantry 104 and/or moving guide member 112b/112c having radiation source 102/102a/102b coupled thereto.

In some embodiments, rotation in the first path about first rotational axis 122 and rotation in the second path about second rotational axis 124 may occur simultaneously. For example, radiation source 102 may be simultaneously advanced in both the first and second circular directions, resulting in a spherical or hemispherical helical path.

In some embodiments, each of rotation in the first path and rotation in the second path occur independent of one another. For example, radiation source 102/102a/102b may not rotate about second rotational axis 124 while the guide 112/112a is rotated about first rotational axis 122. Radiation source 102/102a/102b may subsequently rotate to a second position about second rotational axis 124, and guide 112/112a may then be rotated again. Such an embodiment may result in a series of adjacent circular paths of the radiation source, resulting in an effective spherical or hemispherical path of the radiation source.

In one embodiment, moving the radiation source may include varying the rate of movement/rotation of the radiation source along the guide and/or rotation of the guide. Moving the radiation source may include varying the rate of movement of radiation source 102/102a/102b based on its location such that the radiation intensity is substantially constant along substantially all locations a given radius from isocentric center point 110/and/or treatment area 106. In one embodiment, rotation of guide 112/112a is held at a constant rate and the rate of movement of the radiation source 102/102a/102b about second rotational axis 124 is varied based on its position. For example, as described above, a rate of movement of radiation source 102/102a/102b about second rotational axis 124 may be determined and employed based on equations (1) and (2) described above.

Method 200 illustrates an exemplary series of method steps. Other embodiments may include the addition of steps, the exclusion of steps, and/or the rearrangement of steps described herein. For example, the radiation source(s) may be moved prior to their activation.

Figure 9:
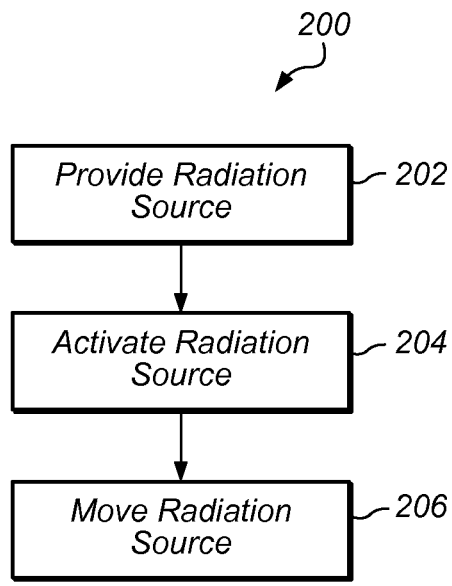
FIG. 9 is a flow chart that illustrates a method of irradiation in accordance with embodiments of the present technique.
Figure 10:
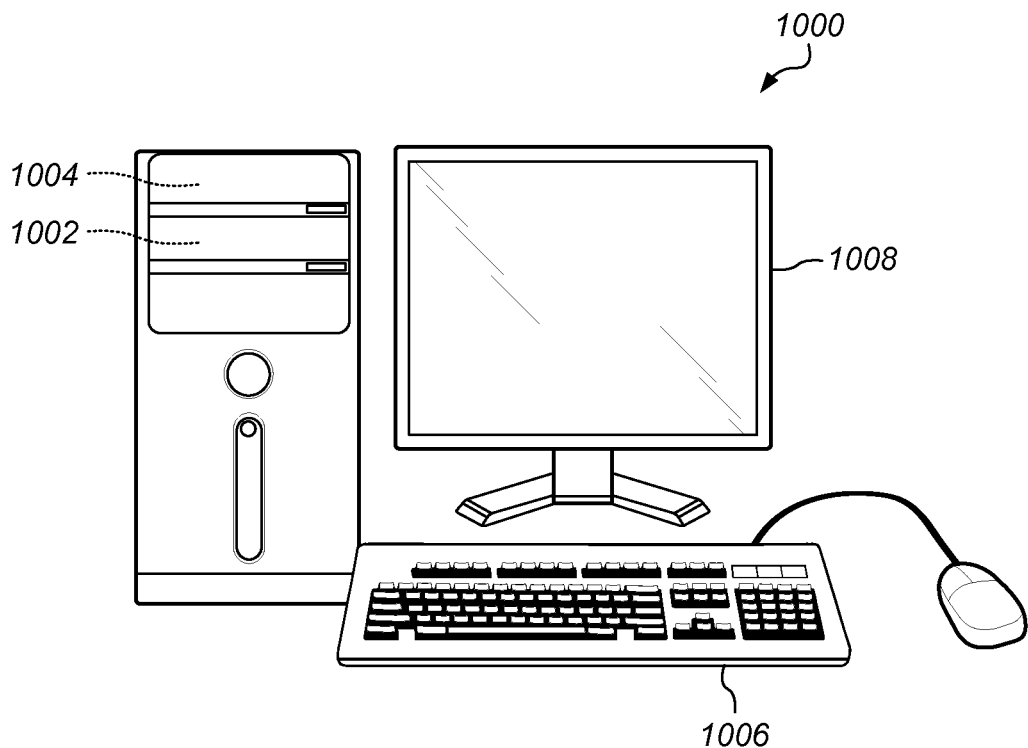
FIG. 10 is a diagram that illustrates a controller in accordance with one or more embodiments of the present technique.

In some embodiments systems 100-100"" may include a controller. A controller may be implemented to control various operational aspects of system 100, such as the rate of movement of source 102 and/or the revolution rate of guides 112, 112a, 112b and/or 112c. FIG. 10 illustrates a controller 1000 in accordance with one or more embodiments of the present technique. Controller 1000 may include a computer or similar device that controls one or more operational aspects of system 100. Controller 1000 may control generation of radiation from radiation source 102 (e.g., radiation intensity), movement of radiation source 102/102a/102b, movement/rotation of guides 112/112a/112b/112c, operation of drives 114, the acquisition of data, and the like. In some embodiments, controller 1000 includes a processor 1002, a memory 1004, peripheral devices 1006, and graphical display 1008. Processor 1002 may include a computer processing unit that is capable of executing various computer implemented routines, such as program instructions stored on memory 1004. Memory 1004 may include a non-transitory computer readable storage medium, such as a hard-disk, floppy-disk, random access memory (RAM), or the like. Memory 1004 may have computer executable instructions/routines stored thereon for the execution of one or more methods in accordance with one or more embodiments of the techniques described herein. Execution of the routines may cause controller 1004 to perform one or more of the method steps described herein. For example, memory 1004 may include program instructions for activating and moving radiation source 102/102a/102b as described above with respect to FIG. 9.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. The words "include", "including", and "includes" mean including, but not limited to. As used throughout this application, the singular forms "a", "an" and "the" include plural referents unless the content clearly indicates otherwise. Thus, for example, reference to "a radiation source" includes a combination of two or more radiation sources. The term "coupled" means "directly or indirectly connected".

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

What is claimed is:

1. A method of radiotherapy, comprising:
activating a radiation source having a radiation path that intersects a treatment area;
moving the radiation source in three dimensions about the treatment area, wherein the radiation source is continually directed substantially toward an isocentric point within the treatment area;
moving the radiation source in a first substantially arched path about a first rotational axis passing through the isocentric point such that a radiation path of the radiation source continues to be directed substantially toward the isocentric point; and
moving the radiation source in a second substantially arched path about a second rotational axis passing through the isocentric point and substantially normal to the first rotational axis such that a radiation path of the radiation source continues to be directed substantially toward the isocentric point;
wherein the rate of movement of the radiation source along the second substantially
arched path about the second rotational axis is about:

$$\text{Rate} = S * \frac{1}{\sin\theta} \text{ or Rate} = S * \frac{1}{\cos\theta}$$

wherein theta (θ) comprises an angle of the location of the radiation source on the second substantially arched path relative to the first rotational axis, wherein phi (φ) is equal to a complementary angle of θ (90−θ), and wherein S is a speed of the radiation source at the given location where the angle is θ or φ, respectively.

2. The method of claim 1, wherein moving the radiation source in the first and second substantially arched paths occurs substantially simultaneously.

3. The method of claim 1, wherein moving the radiation source in the first substantially arched path comprises rotating a guide/gantry supporting the radiation source such that the radiation source moves in a substantially circular path about the first rotational axis.

4. The method of claim 3, wherein the second rotational axis is fixed relative to the guide/gantry such that the second axis rotates in coordination with rotation of the guide/gantry about the first axis.

5. The method of claim 3, wherein the guide/gantry comprises a substantially circular arched shape about the second rotational axis, and wherein moving the radiation source in the second substantially arched path comprises advancing the radiation source lengthwise along the arch shaped guide/gantry such that the radiation source moves in a substantially arched path along the arch shaped guide/gantry and about the second rotational axis.

6. The method of claim 3, wherein the guide/gantry comprises a first member rotatable about the first axis during use, and a second member rotatable about the second axis during use, wherein second member comprises the radiation source coupled thereto, and wherein moving the radiation source in the second substantially arched path comprises rotating the second member about the second axis.

7. The method of claim 1, wherein moving the radiation source in the substantially arched path comprises varying the rate of movement of the radiation source based on the location of the radiation source on the substantially arched path such that the radiation intensity is substantially constant along substantially all locations a given radius from the isocentric center point.

8. The method of claim 1, wherein theta (θ) comprises an angle of the location of the radiation source on the second substantially arched path relative to the first rotational axis, wherein phi (φ) is equal to a complementary angle of θ (90−θ) wherein the rate of movement of the radiation source is provided such that the time spent by the radiation source at an angular position (θ or φ) along the second substantially arched path is directly proportional to the value of sine (θ) or cosine (φ), respectively.

9. The method of claim 1, wherein moving the radiation source further comprises maintaining the radiation source at a substantially constant distance from the isocentric point during movement of the radiation source.

10. An irradiation system, comprising:
a radiation source having a radiation path that intersect an isocentric point and/or treatment area during use;
a supporting structure that, during use, moves the radiation source in three dimensions about the treatment area, wherein the radiation source is continually directed substantially toward an isocentric point within the treatment area;
moves the radiation source in a first substantially arched path about a first rotational axis passing through the isocentric point such that a radiation path of the radiation source continues to be directed substantially toward the isocentric point; and moves the radiation source in a second substantially arched path about a second rotational axis passing through the isocentric point and substantially normal to the first rotational axis such that a radiation path of the radiation source continues to be directed substantially toward the isocentric point;
wherein the rate of movement of the radiation source along the second substantially arched path about the second rotational axis is about:

$$\text{Rate} = S * \frac{1}{\sin\theta} \text{ or Rate} = S * \frac{1}{\cos\phi}$$

wherein theta (θ) comprises an angle of the location of the radiation source on the second substantially arched path relative to the first rotational axis, wherein phi (φ) is equal to a complementary angle of θ (90−θ), and wherein S is a speed of the radiation source at the given location where the angle is θ or φ, respectively.

11. The system of claim 10, wherein the supporting structure moves the radiation source in the first and second substantially arched paths substantially simultaneously.

12. The system of claim 10, wherein the supporting structure moves the radiation source in the first substantially arched path via rotating a guide/gantry supporting the radiation source such that the radiation source moves in a substantially circular path about the first rotational axis.

13. The system of claim 12, wherein the second rotational axis is fixed relative to the guide/gantry such that the second axis rotates in coordination with rotation of the guide/gantry about the first axis.

14. The system of claim 12, wherein the guide/gantry comprises an arched shape about the second rotational axis, and wherein moving the radiation source in the second substantially arched path comprises advancing the radiation source lengthwise along the arch shaped guide/gantry such that the radiation source moves in a substantially arched path along the arch shaped guide/gantry and about the second rotational axis.

15. The system of claim 12, wherein the guide/gantry comprises a first member rotatable about the first axis during use, and a second member rotatable about the second axis during use, wherein second member comprises the radiation source coupled thereto, and wherein moving the radiation source in the second substantially arched path comprises rotating the second member about the second rotational axis.

16. The method of claim 10, wherein moving the radiation source in the substantially arched path comprises varying the rate of movement of the radiation source based on the location of the radiation source on the substantially arched path such that the radiation intensity is substantially constant along substantially all locations a given radius from the isocentric center point.

17. The method of claim 10, wherein theta (θ) comprises an angle of the location of the radiation source on the second substantially arched path relative to the first rotational axis, wherein phi (φ) is equal to a complementary angle of θ (90−θ) wherein the rate of movement of the radiation source is provided such that the time spent by the radiation source at an angular position (θ or φ) along the second substantially arched path is directly proportional to the value of sine (θ) or cosine (φ), respectively.

18. The system of claim 10, wherein the supporting structure maintains the radiation source at a substantially constant distance from the isocentric point during movement of the radiation source.

19. A non-transitory computer readable medium storing program instructions that, when executed by a computer, are configured to cause:
activating a radiation source having a radiation path that intersects a treatment area;
moving the radiation source in three dimensions about the treatment area, wherein the radiation source is continually directed substantially toward an isocentric point within the treatment area;
moving the radiation source in a first substantially circular path about a first rotational axis passing through the isocentric point such that a radiation path of the radiation source continues to be directed substantially toward the isocentric point; and
moving the radiation source in a second substantially circular path about a second rotational axis passing through the isocentric point and substantially normal to the first rotational axis such that a radiation path of the radiation source continues to be directed substantially toward the isocentric point
wherein the rate of movement of the radiation source along the second substantially arched path about the second rotational axis is about:

$$\text{Rate} = S * \frac{1}{\sin\theta} \text{ or } \text{Rate} = S * \frac{1}{\cos\phi}$$

wherein theta (θ) comprises an angle of the location of the radiation source on the second substantially arched path relative to the first rotational axis, wherein phi (φ) is equal to a complementary angle of θ (90−θ), and wherein S is a speed of the radiation source at the given location where the angle is θ or φ, respectively.

20. The medium of claim 19, wherein moving the radiation source in the first and second substantially circular paths occurs substantially simultaneously.

21. The medium of claim 19, wherein moving the radiation source in the substantially arched path comprises varying the rate of movement of the radiation source based on the location of the radiation source on the substantially arched path such that the radiation intensity is substantially constant along substantially all locations a given radius from the isocentric center point.

22. The method of claim 19, wherein theta (θ) comprises an angle of the location of the radiation source on the second substantially arched path relative to the first rotational axis, wherein phi (φ) is equal to a complementary angle of θ (90−θ) wherein the rate of movement of the radiation source is provided such that the time spent by the radiation source at an angular position (θ or φ) along the second substantially arched path is directly proportional to the value of sine (θ) or cosine (φ), respectively.

23. The medium of claim 19, wherein moving the radiation source further comprises maintaining the radiation source at a substantially constant distance from the isocentric point during movement of the radiation source.

* * * * *